(12) United States Patent
Kwon et al.

(10) Patent No.: US 9,328,059 B2
(45) Date of Patent: May 3, 2016

(54) PHARMACEUTICAL COMPOSITION FOR PREVENTING OR TREATING AUTOPHAGY-RELATED DISEASES, ANGIOGENIC DISEASES OR MELANIN-RELATED DISEASES

(75) Inventors: Ho Jeong Kwon, Seoul (KR); Yoon Sun Cho, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 13/990,301

(22) PCT Filed: Sep. 6, 2011

(86) PCT No.: PCT/KR2011/006581
§ 371 (c)(1),
(2), (4) Date: May 29, 2013

(87) PCT Pub. No.: WO2012/074187
PCT Pub. Date: Jun. 7, 2012

(65) Prior Publication Data
US 2013/0251654 A1    Sep. 26, 2013

(30) Foreign Application Priority Data
Nov. 30, 2010    (KR) .................. 10-2010-0120398

(51) Int. Cl.
A61K 8/41     (2006.01)
A61Q 19/02    (2006.01)
C07C 211/42   (2006.01)
A61K 31/135   (2006.01)

(52) U.S. Cl.
CPC ............... *C07C 211/42* (2013.01); *A61K 8/41* (2013.01); *A61K 31/135* (2013.01); *A61Q 19/02* (2013.01)

(58) Field of Classification Search
CPC ........ A61K 31/135; A61K 8/41; A61Q 19/02
See application file for complete search history.

(56) References Cited

U.S. PATENT DOCUMENTS

2007/0270428 A1 * 11/2007 Hagan et al. .................. 514/248
2009/0076019 A1    3/2009 Tyers et al.

FOREIGN PATENT DOCUMENTS

WO    WO-98/06689         2/1998
WO    WO-2009/036275 A1   3/2009

OTHER PUBLICATIONS

Pollard et al., Cell Stem Cell, 4, 568-580, 568-580.*
Melle et al., Cardiovascular Drugs and Therapy, 2004, 18, 441-447.*
Johns Hopkins: Coronary Artery Disease, 1 page, www.hopkinsmedicine.org/heart_vascular_institute/conditions_treatments/conditions/coronary_artery.html.*
International Search Report for PCT/KR2011/006581, mailed Apr. 4, 2012 (3 pages).

* cited by examiner

*Primary Examiner* — Kyle Purdy
(74) *Attorney, Agent, or Firm* — Clark & Elbing LLP; Susan M. Michaud

(57) ABSTRACT

The present invention relates to a pharmaceutical composition for preventing or treating autophagy-related diseases, angiogenic diseases or hypermelanosis, comprising: (a) a pharmaceutically effective amount of an indatraline derivative or a pharmaceutically acceptable salt thereof; and a pharmaceutically acceptable carrier. The composition of the present invention effectively induces autophagy of cells, and thus is very effective for preventing or treating autophagy-related diseases. In addition, the composition of the present invention inhibits angiogenesis through the mechanism of inhibiting angiogenesis, invasion and metastasis and inhibits melanogenesis, and thus can also be effective for preventing or treating angiogenic diseases or melanin-related diseases.

6 Claims, 7 Drawing Sheets

Fig. 5 B
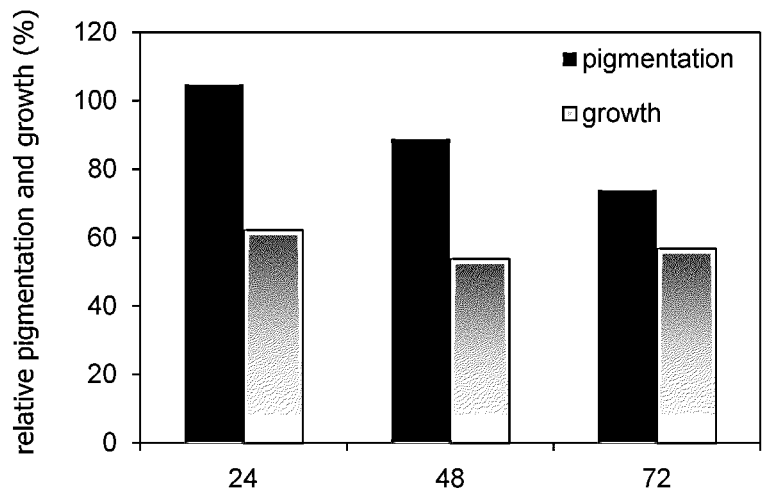
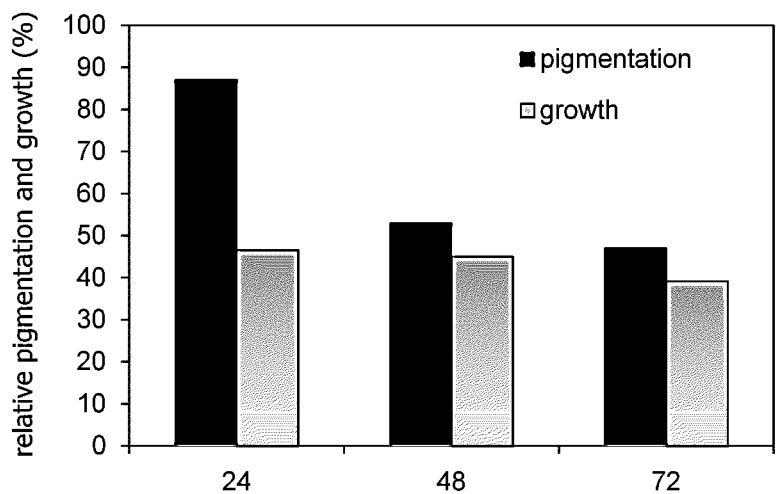

PHARMACEUTICAL COMPOSITION FOR PREVENTING OR TREATING AUTOPHAGY-RELATED DISEASES, ANGIOGENIC DISEASES OR MELANIN-RELATED DISEASES

CROSS-REFERENCE TO RELATED APPLICATIONS

This application is the U.S. national stage filing under 35 U.S.C. §371 of International Application No. PCT/KR2011/006581, filed Sep. 6, 2011, which claims priority from Korean Patent Application 10-2010-0120398, filed Nov. 30, 2010.

FIELD OF THE INVENTION

The present invention relates to a pharmaceutical composition for preventing or treating an autophagy-related disease, an angiogenic disease or a melanin-related disease.

DESCRIPTION OF THE RELATED ART

Autophagy is cell autophagic system that cellular components are degraded to recycle to nutrients and energy sources. During autophagy, malfunctioning organelles and long-lived proteins are collected to become subjects of autophagy. Once autophagy actives, structure of autophagosome membrane is formed by the recruitment of Atg12-Atg5 complex and LC3. The cytosolic form of LC3 (LC3-I) is converted into the membrane-bound form (LC3-II) to mature the autophagosome which enclose the degradation subjects [1, 2]. The autophagosome fuses with a lysosome, resulting in an autolysosome, which degrades any unwanted cellular components. Although this system maintains cellular homeostasis and occurs cell survival or cell death, specific mechanisms of when cell survival or cell death is induced have not yet been unknown. Autophagy-induced cell death is classified as type II cell death and it is irrelevant to caspase-dependent apoptosis [3].

Autophagy is associated with various pathological processes such as neurodegenerative diseases, cancer and melanogenesis [4, 5, 6]. In the case of Parkinson's disease or Alzheimer's disease, fibrils and amyloid plaques are accumulated, which may provide a potential solution for the degradation of these accumulation components. In the case of cancer, autophagy may be associated with various stages [7]. In apoptotic defect cancer cells show defects in apoptosis, autophagy may be induced to promote cell death and regulate cell proliferation. Since oxygen and nutrients are the limited in growing tumor cells, autophagy may be used for survival until the ingredients required are supplied by angiogenesis. At this point, autophagy is suppressed to stop tumor cell survival. Some autophagy inducers coincidentally promote autophagy and apoptosis, which may be a solution to kill cancer cells effectively. Melanogenesis refers to the formation of melanin as a pigment which is found in the eyes, skin and hair. Newly-produced melanin through melanogenesis exhibits different color as compared to melanin commonly present. During melanogenesis, melanosome which is distinct lysosome-related organelles transports functional loading [8]. Therefore, it is reported that melanosome is derived from autophagosome [9]. In addition, in patient with pigmentation disorder, increase of autophagosome was observed, which probably may have been derived from the degradation of immature melanosomes [10]. In recent study, autophagy element was identified as novel regulator of melanogenesis through siRNA-based functional genomics [11]. Pigment accumulation is significantly weakened by deficient of Beclin 1 or LC3-I. In vivo analysis, deficient of Beclin 1 heterozygosity resulted in mouse coat pigmentation defects [12]. Furthermore, melanin plays a role of protection in the skin and eyes, and its loss is related to age-related macular degeneration (AMD) [13, 14]. The brain is also protected by melanin, and its loss causes Parkinson's disease [15]. In addition, melanogenesis is activated by stimulus such as UV external factors [25]. Pigmentation disorders are generated by melanogenesis (chloasma, freckle, age spot, etc.), and abnormality of melanogenesis control can lead to melanoma (skin cancer). Similarly, autophagy is significantly associated with neurodegenerative disorders, cancer and melanogenesis. Therefore, autophagy may be applied to a variety of diseases, whereby it enables autophagy-inducer to become a potential drug candidate.

Throughout this application, several patents and publications are referenced and citations are provided in parentheses. The disclosure of these patents and publications is incorporated into this application in order to more fully describe this invention and the state of the art to which this invention pertains.

DETAILED DESCRIPTION OF THIS INVENTION

Technical Purposes of this Invention

The present inventors have made intensive studies to develop a novel pharmaceutical composition for preventing or treating an autophagy-related disease. As a result, they have found out that indatraline and its derivative effectively induce autophagy, inhibit angiogenesis by mechanism suppressing capillary formation, invasion and migration, and inhibit melanogenesis.

Accordingly, it is an object of this invention to provide a pharmaceutical composition for preventing or treating an autophagy-related disease, an angiogenic disease or a hypermelanosis, comprising indatraline or its derivative.

Other objects and advantages of the present invention will become apparent from the detailed description to follow taken in conjugation with the appended claims and drawings.

Technical Solutions of this Invention

In one aspect of the present invention, there is provided a pharmaceutical composition for preventing or treating an autophagy-related disease, an angiogenic disease or a hypermelanosis, comprising (a) a pharmaceutically effective amount of a compound represented by the following Chemical formula 1 or a pharmaceutically acceptable salt thereof; and (b) a pharmaceutically acceptable carrier:

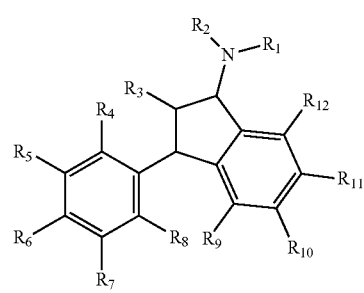

Chemical formula 1 wherein, each of $R_1$, $R_2$ and $R_3$ is independently hydrogen, hydroxy, $C_1$-$C_6$ alkyl, $C_1$-$C_6$ alkenyl and $C_3$-$C_8$ cycloalkyl or $C_1$-$C_6$ alkoxy, and each of $R_4$ to $R_{12}$ is independently hydrogen, halogen, hydroxy, $C_1$-$C_6$ alkyl, $C_1$-$C_6$ alkenyl and $C_3$-$C_8$ cycloalkyl or $C_1$-$C_6$ alkoxy.

In another aspect of the present invention, there is provided a method for preventing or treating an autophagy-related disease, an angiogenic disease or a hypermelanosis, comprising administering to a subject in need thereof a pharmaceutical composition comprising (a) a pharmaceutically effective amount of a compound represented by the following Chemical formula 1 or a pharmaceutically acceptable salt thereof; and (b) a pharmaceutically acceptable carrier.

The present inventors have made intensive studies to develop a novel pharmaceutical composition for preventing or treating an autophagy-related disease. As a result, they have found out that indatraline and its derivative effectively induce autophagy, inhibit angiogenesis by mechanism suppressing capillary formation, invasion and migration, and inhibit melanogenesis.

The term used herein "alkyl" refers to a saturated, substituted or unsubstituted hydrocarbon radical, which may be straight or branched. For example, it includes methyl, ethyl, propyl, isobutyl, pentyl, hexyl, etc. $C_1$-$C_6$ alkyl means an alkyl group having an alkyl unit of 1-6 carbon atoms. In the Chemical formula 1, $C_1$-$C_6$ alkyl at the $R_1$, $R_2$ or $R_3$ position is preferably $C_1$-$C_3$ alkyl.

The term used herein "cycloalkyl" refers to a cyclic hydrocarbon radical, which includes cyclopropyl, cyclobutyl, cyclopentyl. $C_3$-$C_8$ cycloalkyl means cycloalkyl with a ring structure consisting of 3 to 8 carbon atoms. When the $C_3$-$C_8$ cycloalkyl is substituted, the number of carbons in the substituent is not included.

The term used herein "alkenyl" refers to an unsaturated, substituted or unsubstituted hydrocarbon radical having a specified number of carbons, which may be straight or branched. For example, it includes ethenyl, vinyl, propenyl, allyl, isopropenyl, butenyl, isobutenyl, t-butenyl, n-pentenyl and n-hexenyl. In Chemical Formula 1, the $C_1$-$C_6$ alkenyl means an alkenyl group having an alkenyl unit of 1-6 carbon atoms. When the $C_1$-$C_6$ alkenyl is substituted, the number of carbons in the substituent is not included.

The term used herein "halogen" refers to a halogen element. For example, it includes fluoro, chloro, bromo and iodo.

According to a preferred embodiment, in indatraline derivative of the Chemical formula 1, each of $R_1$, $R_2$ and $R_3$ is independently hydrogen or $C_1$-$C_3$ alkyl, and each of $R_4$ to $R_{12}$ is independently hydrogen, $C_1$-$C_3$ alkyl or halogen.

More preferably, the present indatraline derivative is represented by the following Chemical formula 2:

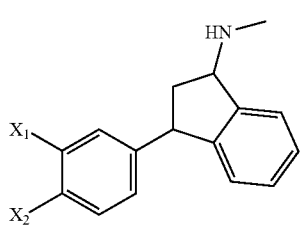

Chemical formula 2 wherein, each of $X_1$ and $X_2$ is independently halogen.
Still more preferably, in the Chemical formula 2, each of $X_1$ and $X_2$ is chlorine atom (Cl).

The present compounds may have one or more chiral center and/or geometrical isomerism center such that the present invention includes all stereoisomers (i.e., optical isomers, diastereomers and geometrical isomer) represented by the Chemical formula 1 or the Chemical formula 2.

The present indatraline derivative is very effective for preventing or treating an autophagy-related disease. The autophagy-related disease is diseases which are treatable by inducing autophagy. Specifically, it means all treatable diseases that autophagy inhibits growth and differentiation of cells, decreases mutagenesis or eliminates cell organelle (e.g., mitochondria) damaged by reactive oxide. For example, the autophagy-related disease includes cancer, atherosclerosis, Alzheimer's disease, Parkinson's disease, amyotrophic lateral sclerosis, Huntington's disease, spinocerebellar ataxia, oculopharyngeal muscular dystrophy, prion disease, Fatal familial insomnia, alpha-1-antitrypsin deficiency, dentatorubral pallidoluysian atrophy, frontotemporal dementia, progressive supranuclear palsy, x-linked spinobulbar muscular atrophy and neuronal intranuclear hyaline inclusion disease.

Specifically, for example, cancer may be pituitary adenoma, neuroglioma, brain tumor, epipharyngeal carcinoma, laryngeal cancer, thymoma, mesothelioma, breast cancer, lung cancer, stomach cancer, esophageal cancer, colon cancer, liver cancer, pancreatic cancer, pancreatic endocrine tumors, gallbladder cancer, penile cancer, ureteral cancer, renal cell carcinoma, prostate cancer, bladder cancer, non-Hodgkin's lymphoma, myelodysplastic syndrome, multiple myeloma, plasma cell tumors, leukemia, paediatric cancer, skin cancer, ovarian cancer or cervical cancer, preferably cervical cancer.

In addition, the present indatraline derivative is very effective for preventing or treating an angiogenic disease since indatraline derivative inhibits angiogenesis by mechanism suppressing capillary formation, invasion and migration. The angiogenic disease means diseases caused by angiogenesis. For example, it includes cancer, stenosis, restenosis, diabetic retinopathy, retinopathy of prematurity, corneal transplant rejection, neovascular glaucoma, erythrosis, proliferative retinopathy, psoriasis, hemophilic arthropathy, proliferation of capillaries in atherosclerotic plaques, keloid, wound granulation, vascular adhesion, rheumatoid arthritis, osteoarthritis, autoimmune disease, Crohn's disease, atherosclerosis, intestinal tract adhesion, cat scratch disease, ulcer, hepatocirrhosis, glomerulonephritis, diabetic nephropathy, malignant nephrosclerosis, thrombotic microangiopathy, organ transplant rejection, glomerulopathy, diabetes, inflammation or neurodegerative disease, but is not limited thereto.

Specifically, for example, cancer may be pituitary adenoma, neuroglioma, brain tumor, epipharyngeal carcinoma, laryngeal cancer, thymoma, mesothelioma, breast cancer, lung cancer, stomach cancer, esophageal cancer, colon cancer, liver cancer, pancreatic cancer, pancreatic endocrine tumors, gallbladder cancer, penile cancer, ureteral cancer, renal cell carcinoma, prostate cancer, bladder cancer, non-Hodgkin's lymphoma, myelodysplastic syndrome, multiple myeloma, plasma cell tumors, leukemia, paediatric cancer, skin cancer, ovarian cancer or cervical cancer, preferably cervical cancer.

In addition, the present indatraline derivative is very effective for inhibiting metastasis of cancer by inducing autophagy of cancer cell, inhibiting angiogenesis or suppressing capillary formation, invasion and migration to exhibit excellent anticancer effects.

The present indatraline derivative inhibits angiostenosis. It is presumed that stenosis in blood vessels due to the formation of thrombus or new endangium after damage of vascular endothelial cells. Specifically, it is presumed that platelet is adhered to the vessel wall by damage of vascular endothelial cells to form thrombus, or migration and proliferation of smooth muscle cells is occurred by generation of growth factor to form new endangium, whereby blood vessel is narrowed.

A disease based on the stenotic vascular lesion includes restenosis after blood vessel disorder by PTCA (percutaneous transluminal coronary angioplasty), unstable angina, acute myocardial infarction, transient ischemic attack or chronic arterial occlusion, but is not limited thereto.

Most of angina is based on coronary atherosclerosis. It is caused by local ischemia result from imbalance in myocardial oxygen demand and supply.

Depending on the form of attack, it is divided into stable angina and unstable angina. Unstable angina means angina recurring after asymptomatic period of more than six months, and exertional angina newly occurring within 3-4 weeks. In addition, 50-80% of those are advanced to acute myocardial infarction.

Acute myocardial infarction is the state that blood flow is occlusived by advanced angina, whereby the heart muscle is starved for a sufficient amount of oxygen to cause necrosis.

Although transient ischemic attack shows the same symptoms of cerebral infarction, it is transient.

ASO (arteriosclerosis obliterans) is a representative of chronic arterial occlusion. The ASO is based on sclerosis of the arteries. It shows ischemic symptoms according to reduction of blood flow by arterial stenosis or occlusion.

In addition, the present indatraline derivative is very effective for preventing or treating a hypermelanosis since it inhibits melanogenesis.

The relation between autophagy and melanogenesis has been reported so far that autophagy is increased by formation of melanosome in melanogenesis and occurred for cell survival in melanocyte. However, the present indatraline or its derivative has efficacy which induces autophagy and inhibits melanogenesis at the same time, suggesting that a new relation between autophagy and melanogenesis. That is to say, autophagy induction by therapeutic effects of indatraline or its derivative in melanocyte (not naturally occurring autophagy in melanogenesis) leads to suppression of melanogenesis by inhibiting cell growth rather than cell survival. This autophagy mechanism may be exhibited by effects as inhibitor of neurotransmitter reuptake which is active mechanism of indatraline or its derivative. Neurotransmitter epinephrine has been already reported to induce melanogenesis (Hu, D-N, et al., Influence of autonomic neurotransmitters on human uveal melanocytes in vitro. *Exp. Eye Res.,* 71: 217-224 (2000)). In addition, epinephrine has been already reported to inhibit autophagy by its activity (Seglen, P. O. et al., Autophagy and other vacuolar protein degradation mechanisms. *Experientia,* 48:158-172 (1992)). i.e., it is supposed that autophagy induction and melanogenesis inhibitory effects of indatraline or its derivative compound are exhibited by inhibiting intracellular penetration amounts of epinephrine. Therefore, the present indatraline or its derivative may suggest a new correlation between autophagy and melanogenesis.

The present indatraline or its derivative compound may be used for preventing or treating a hypermelanosis since it inhibits effectively melanogenesis as described above.

The hypermelanosis includes chloasma, freckle, age spot, blemish, epidermal melanocytic lesion, Cafe's au lait macules, Becker's Nevus, Nevus Spilus, Lentigines, dermal melanocytic lesions, Mongolian spot, Nevus of Ota, Acquired bilateral nevus of Ota-like macules, Nevus of Ito, Blue nevus, Melanocytic nevus, Junctional nevus, Compound nevus, Intradermal nevus, Halo nevus, Congenital nevocytic nevus, Spitz nevus, Dysplastic nevus, Melanoma, Lentigo maligna melanoma, Superficial spreading melanoma, Acral lentiginous melanoma, Nodular melanoma, pigment basal cell carcinoma, dermatofibromas, dermoid cyst, keloid and keratoacanthomas, but is not limited thereto.

In the composition of the present invention, the present indatraline derivative may include not only the above-described compounds of Chemical formula 1 or Chemical formula 2 but also a pharmaceutically acceptable salt thereof. The term used herein "pharmaceutically acceptable salt" refers to a form of the compound which does not cause serious irritation to an organism administered and not impair biological activities and properties of the compound. For example, it includes ammonium salts, alkali metallic salts, alkali earth metals, transition metal salts, quaternary amine salts, amino acids salts, but is not limited thereto. The term "pharmaceutically effective amount" as used herein means an amount sufficient to achieve the pharmaceutical effect for treating as described above.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, stearate, magnesium and mineral oils.

The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995).

The pharmaceutical composition according to the present invention may be administered orally or parenterally. For parenteral administration, it may be administered intravenously, subcutaneously, intramusculerly, intraperitoneally and transdermally.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition. Preferably, pharmaceutical composition of the present invention may be administered with a daily dosage of 0.001-100 mg/kg (body weight).

According to the conventional techniques known to those skilled in the art, the pharmaceutical composition according to the present invention may be formulated with pharmaceutically acceptable carrier and/or vehicle as described above, finally providing several forms including a unit dose form and a multi-dose form. Non-limiting examples of the formulations include, but not limited to, a solution, a suspension or an emulsion in oil or aqueous medium, an elixir, a powder, a granule, a tablet and a capsule, and may further comprise a dispersion agent or a stabilizer.

In another aspect of the present invention, there is provided a cosmetic composition for whitening skin, comprising a compound represented by the following Chemical formula 1 or a salt thereof:

Chemical formula 1

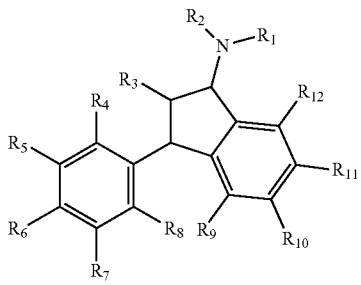

wherein, each of $R_1$, $R_2$ and $R_3$ is independently hydrogen, hydroxy, $C_1$-$C_6$ alkyl, $C_1$-$C_6$ alkenyl and $C_3$-$C_8$ cycloalkyl or $C_1$-$C_6$ alkoxy, and each of $R_4$ to $R_{12}$ is independently hydrogen, halogen, hydroxy, $C_1$-$C_6$ alkyl, $C_1$-$C_6$ alkenyl and $C_3$-$C_8$ cycloalkyl or $C_1$-$C_6$ alkoxy.

In still another aspect of the present invention, there is provided a method for whitening skin, comprising topically applying to a skin of a subject in need thereof a composition comprising a compound represented by the Chemical formula 1 or salt thereof.

Since the present cosmetic composition for whitening skin uses the composition comprising a compound represented by the Chemical formula 1 or salt thereof as an active ingredient, the common descriptions between them are omitted in order to avoid undue redundancy leading to the complexity of this Specification.

The present cosmetic composition shows an effect for whitening skin since it effectively inhibits melanogenesis. The effect for whitening skin includes prevention or improvement for chloasma, freckle, age spot and blemish, but is not limited thereto.

Where the composition of the present invention is prepared as a cosmetic composition, the composition of the present invention includes the compound represented by the Chemical formula 1 or salt thereof as the active ingredient, and also the components that are generally used in the cosmetic composition, in which the components include for example, general adjurvants, such as an antioxidant, a stabilizer, a dissolving agent, vitamins, pigments, and flavouring, and carriers.

As the carriers, purified water, monovalent alcohols (ethanol or propyl alcohol), polyvalent alcohols (glycerol, 1,3-butylene glycol, or propylene glycol), high fatty acids (palmitic acid or linolenic acid), fats (wheat germ oil, camellia oil, jojoba oil, olive oil, squalene, sunflowers oil, *macadamia* nuts oil, avocado oil, soybean water-added lecithin, or fatty acid glyceride), and the like may be used, but the present invention is not limited thereto. In addition, if necessary, a surfactant, an antimicrobial agent, an antioxidant, an ultraviolet ray adsorbent, anti-inflammatory, and a refrigerant may be added.

The surfactant may include one selected from the group consisting of polyoxy ethylene, hydrogenated castor oil, polyoxy ethylene, oleyl ether, monooleic acid polyoxyethylene, polyoxy ethylene, glyceryl monostearate, monostearic acid sorbitan, monooleic acid polyoxy ethylene, sorbitan, sucrose fatty acid ester, monolauric acid hexaglycerin, polyoxy ethylene reduced lanolin, POE, glyceryl pyroglutamic acid, isostearic acid, diester, N-acetylglutamin, and isostearyl ester.

The antimicrobial agent may include one selected from the group consisting of hinokithiol, triclosan, chlorhexidine gluconic acid salt, phenoxy ethanol, resorcin, isopropylmethylphenol, azulene, salicylic acid, and zincpyritaon.

As the antioxidant, any one from butylhydroxyanisol, gallic acid, propyl gallate, and erythorbate may be available.

As the ultraviolet ray absorbent, any one from benzophenones such as dihydroxybenzophenone, melanin, paraminobenzoic acid ethyl, paradimethyl aminobenzoic acid 2-ethylhexyl ester, cynocite, paramethoxy cinnamic acid 2-ethylhexylester, 2-(2-hydroxy-5-methylphenyl)benzotriazole, urocanic acid, and metallic oxide particles may be available.

As the anti-inflammatory, glythylic acid dipotassium or allantoin may be used, and as the refrigerant, *capsicum* tincture or 1-menthol may be used.

In further aspect of the present invention, there is provided a functional cosmetics for whitening skin, comprising cosmetic composition described above.

The cosmetics may be formulated in a wide variety of forms as commonly known in the art, for example, including sun screen cosmetics, solutions, emulsions, essences, creams, peelings, packs, powders, foundations, lipsticks, rouges, eye make-ups, cleansing cosmetics, massage creams and body cosmetics, but is not limited thereto.

Effects of this Invention

The features and advantages of the present invention will be summarized as follows:
(i) The present invention provides a pharmaceutical composition for preventing or treating an autophagy-related disease, an angiogenic disease or a hypermelanosis, comprising (a) a pharmaceutically effective amount of an indatraline derivative or a pharmaceutically acceptable salt thereof; and (b) a pharmaceutically acceptable carrier.
(ii) The composition of the present invention is very effective for preventing or treating autophagy-related diseases since it effectively induces autophagy of cells. In addition, the composition of the present invention inhibits angiogenesis through the mechanism of inhibiting capillary formation, invasion and migration and suppresses melanogenesis, whereby it may be effectively used for preventing or treating an angiogenic disease or a melanin-related disease.

BRIEF DESCRIPTION OF THE DRAWINGS

In FIG. 5A, LC3 conversion was induced by indatraline in B16-F10 and melan-a. In FIG. 5B, indatraline inhibited melanogenesis and cell growth by approximately 74% and 56%, respectively in melan-a cells. In addition, indatraline inhibited melanogenesis and cell growth by approximately 59% and 54%, respectively in B16-F10 cells.

EXAMPLES OF THE INVENTION

Figure 1:
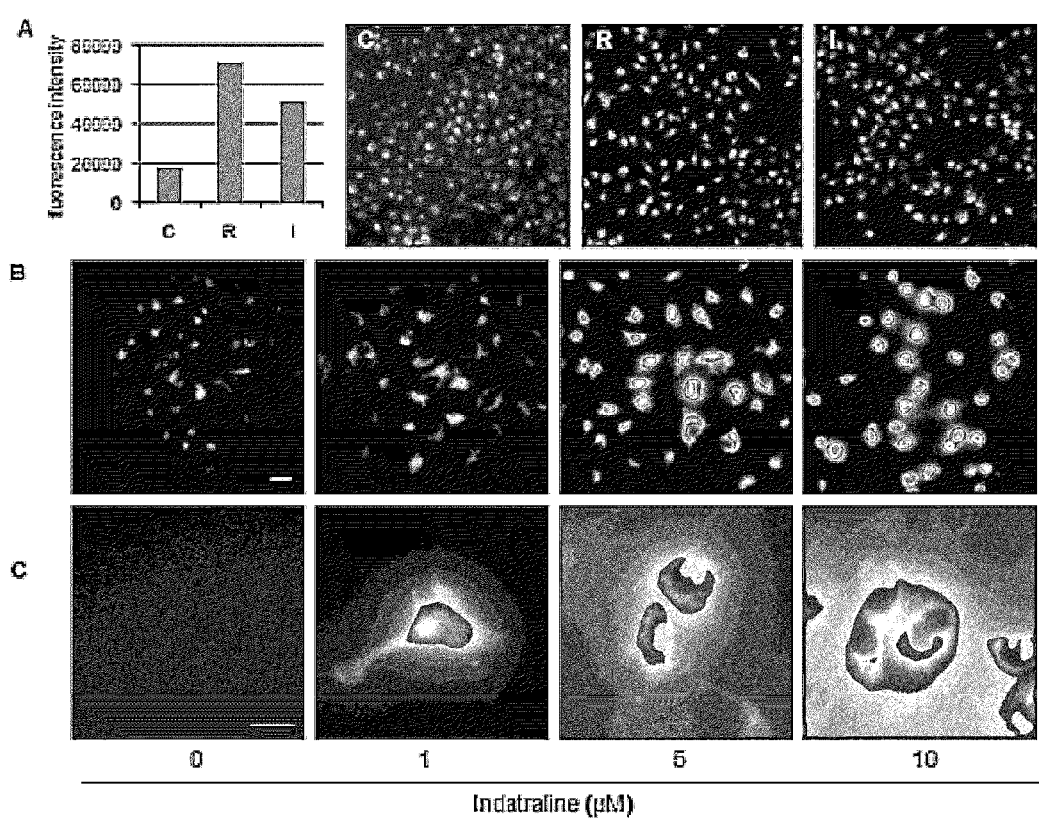
In FIG. 1A, indatraline-induced autophagy was quantified with Lysotracker fluorescence using HCS. Images represent pseudo colors of Lysotracker fluorescence (C: control group, R: rapamycin, I: indatraline).
In FIG. 1B, MDC staining represents results of dose-dependent increase of fluorescence in indatraline-treated cells.
In FIG. 1C, stable cell line expressing EGFP-LC3 showed that EGFP-LC3 fluorescence increased indatraline concentration-dependently in the cytoplasm. The scale bar represents 20 µm.

The present invention will now be described in further detail by examples. It would be obvious to those skilled in the art that these examples are intended to be more concretely illustrative and the scope of the present invention as set forth in the appended claims is not limited to or by the examples.

Examples

Materials and Methods

1. Cell Culture

HeLa (human epithelial cervix adenocarcinoma) cells and COS-7 (African green monkey kidney cells) cells (Korean Cell Line Bank) were grown and maintained in DMEM containing 10% FBS (fetal bovine serum). A stable COS7 cell line expressing EGFP-LC3 was established by transfecting COS7 cells with pEGFP-LC3 using Lipofectamine 2000 according to the manufacturer's protocol (Invitrogen). Stable clones were selected in complete medium containing 750 μg/mL of G418. Cells were cultured at 37° C. in an atmosphere of 5% $CO_2$ in air, pH 7.4. DMEM and FBS were obtained from Gibco Laboratories (Grand Island, N.Y.). Plasmids encoding EGFP-LC3 was kindly provided by Tamotsu Yoshimori (National Institute for Basic Biology, Japan).

2. Autophagy Detection Using Lysotracker, MDC and Stable Cell Line Expressing EGFP-LC3

HeLa cells were cultured up to 70% confluence and then treated with indatraline (Sigma) represented by the following Chemical formula for 24 hrs, followed by treatment with 50 nM of LysoTracker and 50 μM of MDC for 30 min, respectively. Each sample was washed with PBS three times and visualized by fluorescence microscopy. COS7 cells stably expressing EGFP-LC3 were treated with compounds for 24 hrs and then visualized by fluorescence microscopy. Hoechst 33258 and LysoTracker were purchased from Molecular Probes (Eugene, Oreg.), and MDC was purchased from Bio-Chemika (Sigma, Switzerland).

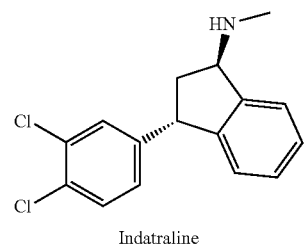 [SMILES: CN[C@@H]1C[C@@H](c2ccc(Cl)c(Cl)c2)c2ccccc21]

Indatraline

3. LC3 Immunoblotting

Soluble proteins were harvested from indatraline-treated HeLa cells by using SDS buffer (50 mM Tris HCl, pH 6.8, 10% glycerol, 2% SDS, 10 mM dithiothreitol, and 0.005% bromophenol blue). Equal volumes of proteins were separated by 12.5% SDS-PAGE and transferred to PVDF membranes (Millipore). Blots were then blocked and immunolabeled overnight at 4° C. using anti-LC3 antibody (MBL, Nagoya, Japan). Immunolabeling was visualized with enhanced chemiluminescence (ECL) kit (Amersham Life Science, Inc., Buckinghamshire, UK) according to the manufacturer's protocol. Tubulin was used as an internal control and was detected using anti-tubulin antibody (Upstate Biotechnology).

4. Cell Proliferation Assay

Cell proliferation was measured using a MTT [3-(4,5-dimethylthiazol-2-yl)-2,5-diphenyltetrazolium bromide] colorimetric assay. HeLa cells and HUVEC (Lonza, USA) were seeded at a density of $3\times10^3$ cells/well in 96-well plates and incubated for 24 hrs. Cells were treated with various concentration of indatraline. After 3 days of treatment, 2 mg/mL MTT was added to each well and incubated for 4 hrs. MTT formazoan in each well was dissolved in 150 μL of DMSO, and absorbance at 595 nm was measured in a microplate reader (Bio-Tek Instrument Inc., Winooski, Vt.). Relative cell growth was measured by calculating the ratio between signal of indatraline-treated wells and control wells.

5. Capillary Formation Assay

Matrigel (10 mg/mL) (BD, USA) was coated to 48-well plates and polymerized at 37° C. HUVEC ($6\times10^4$ cells) was inoculated on the surface of matrigel in 48-well plates. Under the presence of VEGF (50 ng/ml), the compound was added for 4 hrs at 37° C. Cell morphological changes and a capillary structure formed were observed microscope (IX71, Olympus), and the images were obtained using DP70 camera (Olympus) at 100× magnification.

6. Chemoinvasion Assay

In vitro HUVEC invasion was verified using Transwell chamber equipped 8.0-1 m size pore polycarbonate filter insert. Briefly, the lower layer surface of the filter was coated with gelatin (1 mg/mL), and the upper layer surface of the filter was coated with matrigel (3 mg/mL). HUVEC ($7\times10^4$ cells) was placed in the upper layer of the filter, and the compound was added to the lower layer of the filter under the presence of VEGF (50 ng/ml). Then, the chamber was incubated at 37° C. for 18 hrs. The cells were fixed with 70% methanol and stained with hematoxylin and eosin. The lower layer of the filter was observed by microscope with 100× magnification to measure the cell invasion. The cell images were obtained using DP70 camera.

7. Cell Migration Assay

To measure cell migration, HUVEC cells were cultured up to 100% confluence in 12-well plates. Then, the well was wounded a straight scratch using a 200 μL pipette tip. Cells were treated with indatraline and cells migration was observed every 3 hrs. The wound at 9 hrs was recovered by almost 80%. The images were obtained using DP70 camera with 40× magnification.

8. Measurement on Amounts of Melanin Generated

In order to verify whether indatraline induces autophagy and is involved in melanogenesis, skin cancer cell line B16-F10 and normal skin cell line melan-a were treated with indatraline to determine autophagy generation. The amount of melanin generated in each cell line was measured at 5 μM concentration in which autophagy strongly occurs. For measurement on amounts of melanin, cells were treated with indatraline for 24, 48 and 72 hrs, and collected with KOH every day to measure melanin pigment absorbance at 410 nm. At the same time, cell proliferation was measured using MTT. Cell growth inhibition was partially decreased; however, the amount of melanin generated was significantly decreased as time passed.

9. Measurement on Inhibitory Ability to Angiostenosis

In order to verify effects for inhibiting angiostenosis by indatraline as autophagy-induced material in rat carotid artery, a balloon injury was created in the normal left rat carotid artery. After balloon injury, indatraline, rapamycin and DMSO (control group) were treated using catheter to observe angiostenosis. After rapamycin or indatraline treatment, inhibition of angiostenosis caused by proliferation of smooth muscle cells was observed in blood vessel intima. At 7 days after the injury, the carotid arteries were excised. Smooth muscle cells were stained with hematoxylin and eosin (H&E). Levels of angiostenosis were observed.

Result

1. Indatraline Induces Autophagy.

Induction of autophagy by indatraline was measured by Lysotracker and MDC staining. Autophagy induction efficacy of indatraline in Hela cells was quantified by HCS (high contents screening) and Lysotracker fluorescence intensity (FIG. 1A). Lysotracker is a fluorescent dye staining intracellular acidic vacuoles. Induction of autophagy was clearly verified by increase of fluorescence. In HCS, indatraline induced autophagy similar to rapamycin. In addition, autophagy induced by indatraline is 2.87 times stronger than that of control group in 1 μM (FIG. 1A). In addition, Induction of autophagy was verified by MDC (Monodansylcadaverine) staining. Specific autophagy marker MDC stained autophagic vacuoles [17]. MDC staining showed dose-dependent increase of fluorescence from 1 μM (FIG. 1B).

2. Indatraline-Induced Autophagy was Observed in Stable Cell Line Expressing EGFP-LC3.

In order to measure direct elements of autophagy, indatraline-induced autophagy was further verified in stable COST cell line expressing EGFP-LC3. Where autophagy was induced, the cytosolic form of LC3 is converted into the membrane-bound form. By the recruitment of Atg12-Atg5 complex, the cytosolic form of LC3 is converted into the membrane-bound form to mature the autophagosome. After indatraline treatment for 24 hrs, EGFP-LC3 positive small vacuoles were examined in the cytosol. EGFP-LC3 fluorescence increased concentration-dependently in the cytoplasm (FIG. 1C).

2. Indatraline-Induced Autophagy was Observed in Stable Cell Line Expressing EGFP-LC3.

Figure 2:
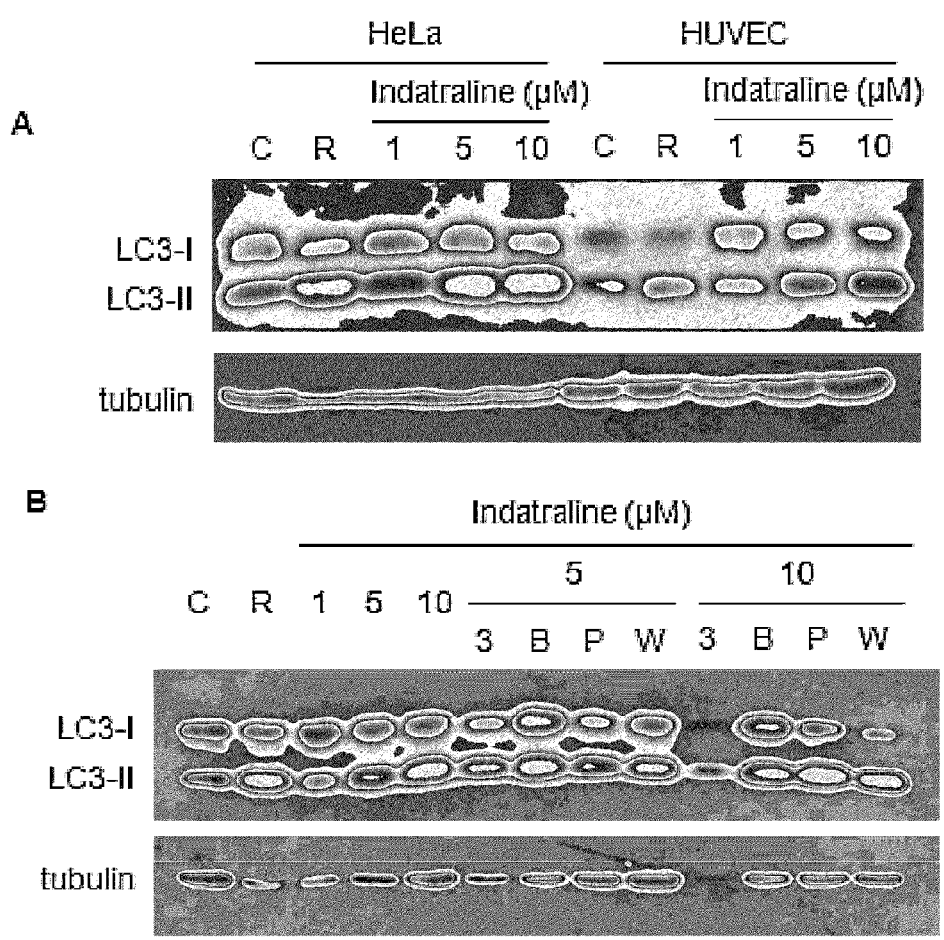
In FIG. 2A, LC3 conversion in HUVEC and HeLa cells were tested in concentration starting from 5 µM.
In FIG. 2B, autophagy inhibitors were pre-treated for 1 hr before indatraline. Where indatraline was treated with 5 µM of concentration, the conversion of LC3-I to LC3-II was inhibited in Bafilomycin A-treated sample and Wortmannin-treated sample. However, where indatraline was treated with 10 µM of concentration, the conversion of LC3-I to LC3-II was inhibited in only Bafilomycin A-treated sample (C: control group, R: rapamycin, 3: 3-MA, B: Bafilomycin A, P: PD98059, W: Wortmannin).

LC3 conversion was finally verified by immunoblotting. After indatraline treatment for 24 hrs, the conversion of LC3-I to LC3-II in cells was tested (FIG. 2A). Inductions of autophagy in both of HUVEC and HeLa cells were tested in concentration starting from 5 μM. In order to investigate signal pathway related to indatraline, well-known autophagy inhibitors 3-MA (10 mM) [18], Bafilomycin A (100 nM) [19], PD98059 (10 μM) [20] and Wortmannin (100 nM) [21] was treated with indatraline. The inhibitors were pre-treated for 1 hr before indatraline and treated with 5 μM or 10 μM of indatraline. Where indatraline was treated with 5 μM of concentration, the conversion of LC3-I to LC3-II was inhibited in Bafilomycin A-treated sample and Wortmannin-treated sample (FIG. 2B). However, where indatraline was treated with 10 μM of concentration, the conversion of LC3-I to LC3-II was not inhibited in inhibitor-treated samples, except for Bafilomycin A-treated sample. Therefore, it would be found that PI3K inhibitor Wortmannin was directly involved in indatraline-induced autophagy signal pathway.

4. Indatraline Inhibits Cell Proliferation.

Figure 3:
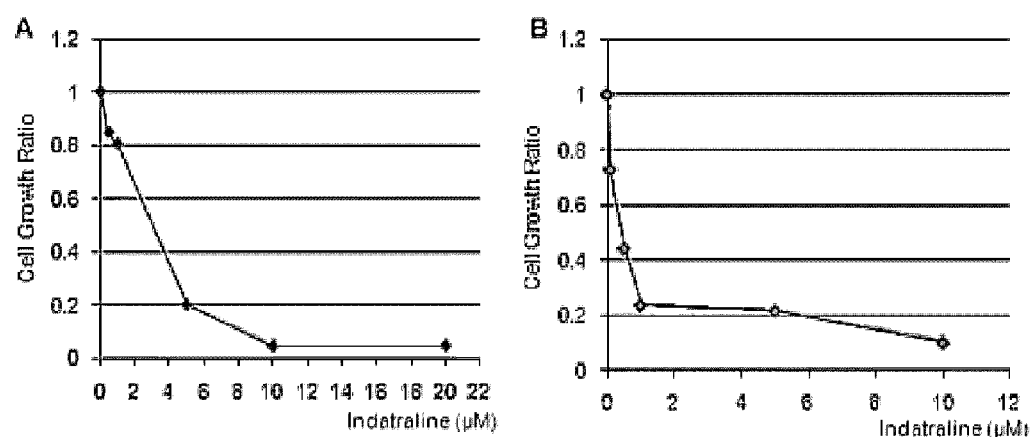
In FIG. 3, indatraline inhibits cell proliferation in both of HeLa and HUVEC. Indatraline inhibited cell proliferation with an $IC_{50}$ of 3 μM in HeLa cell (FIG. 3A) and Indatraline inhibited cell proliferation with an $IC_{50}$ of 0.5 μM in HUVEC (FIG. 3B).

Effect of indatraline in HeLa cell proliferation was examined. After 3 days, it results in significant reduction of cell growth. Indatraline inhibited cell proliferation with an $IC_{50}$ of 3 μM in HeLa cell (FIG. 3A). Cell proliferation inhibition by indatraline was more sensitive in HUVEC (FIG. 3B). Indatraline inhibited cell proliferation with an $IC_{50}$ of 0.5 μM in HUVEC (FIG. 3B). Since indatraline inhibits the growth of HUVEC, anti-angiogenesis efficacy of indatraline was tested.

5. Indatraline Inhibits Anti-Angiogenesis.

Figure 4:
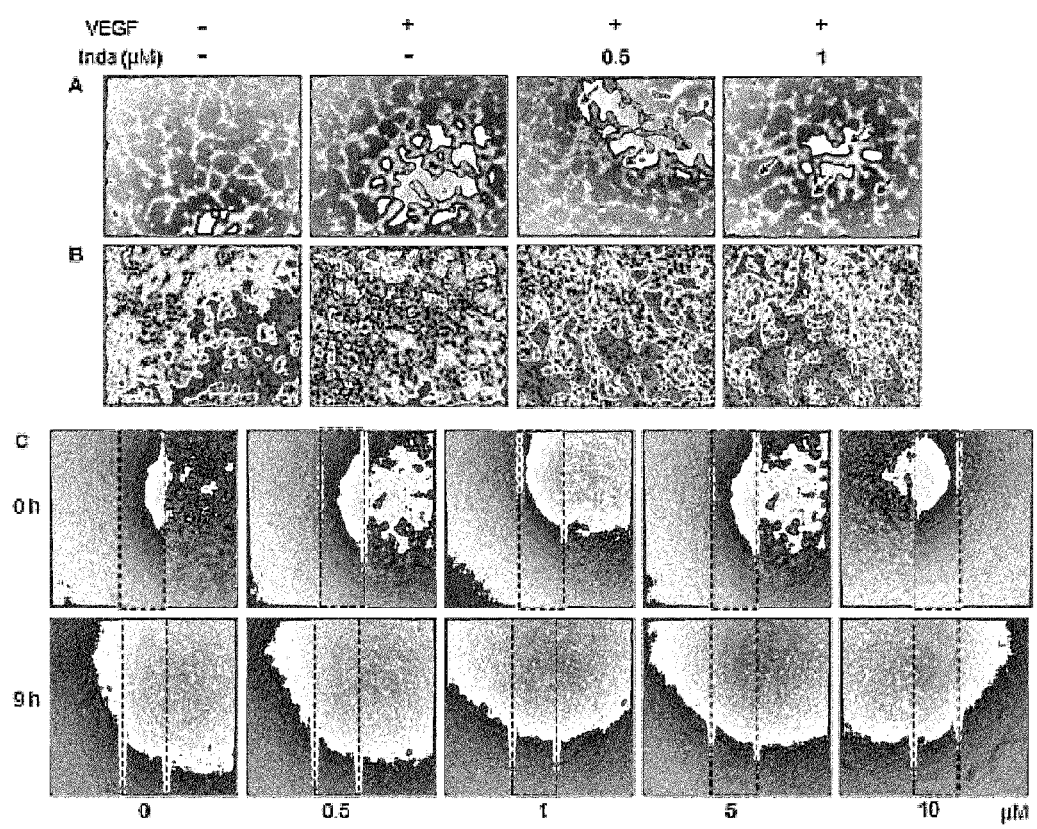
In FIG. 4A, VEGF-induced capillary formation was inhibited by 1 μM of indatraline treatment.
In FIG. 4B, VEGF-induced invasion was effectively inhibited by indatraline concentration starting from 5 μM.
In FIG. 4C, 5 μM and 10 μM of indatraline treatment inhibited migration of HUVEC.

In order to investigate autophagy efficacy and potential for anti-angiogenic agent of indatraline, in vitro angiogenesis assay was conducted. indatraline weakly inhibited a capillary formation which is a network between endothelial cells (FIG. 4A). Although capillary formation was induced by VEGF [22], 1 μM of indatraline treatment inhibited the mature capillary formation. In addition, in order to investigate invasion of angiogenesis, the chemical invasion assay was conducted. Invasion in HUVEC was induced by VEGF, 0.5 μM and 1 μM of indatraline treatment significantly decreased invasion cells (FIG. 4B). In addition, migration assay for indatraline was conducted as metastasis indicator. After 9 hrs, HUVEC was moved to nearly 100% confluence. At this point, 5 μM and 10 μM of indatraline treatment inhibited migration of HUVEC (FIG. 4C). Overall, indatraline inhibited angiogenesis by suppressing capillary formation, invasion and migration. Therefore, indatraline has potential for anti-angiogenic agent inhibiting in vitro angiogenesis.

6. Indatraline Inhibits Melanogenesis.

Figure 5:
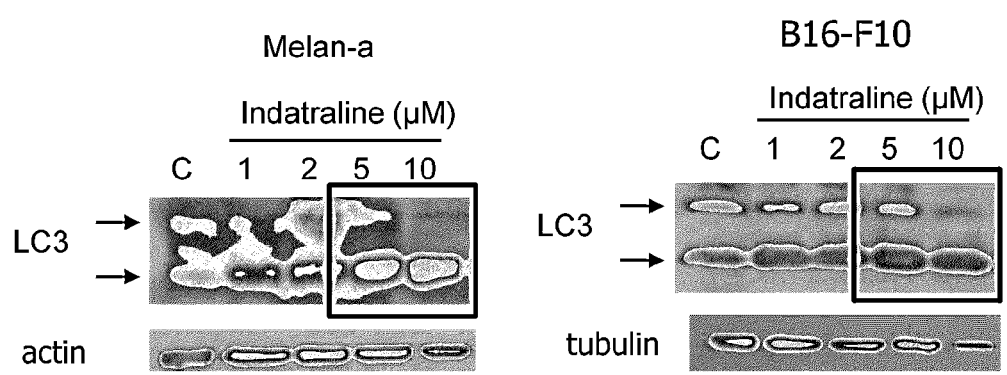

It was verified whether indatraline is induced autophagy and involved in melanogenesis. The correlation of autophagy and melanogenesis has been studied as described above. Pigmentation disorders are generated by melanogenesis (chloasma, freckle, age spot, etc.), and abnormality of melanogenesis control can lead to melanoma (skin cancer). Therefore, melanogenesis control may be used to whitening and skin cancer treatment. Skin cancer cell line B16-F10 and normal skin cell line melan-a were treated with indatraline. As a result, it was determined that autophagy was induced. In B16-F10 cells, autophagy marker LC3 conversion strongly occurred at 5 μM and 10 μM of concentration. In melan-a cells, LC3 conversion was observed from 1 μM of concentration (FIG. 5A).

The amount of melanin generated in each cell line was measured at 5 μM of concentration which autophagy surely occurs. For measurement on amounts of melanin, cells were treated with indatraline for 24, 48 and 72 hrs, and collected with KOH every day to measure melanin pigment absorbance at 410 nm. indatraline inhibited melanogenesis from 48 hrs, as compared to the control group. In melan-a cells, melanogenesis was inhibited by approximately 89% at 48 hrs and approximately 74% at 72 hrs. In B16-F10 cells, melanogenesis was inhibited by approximately 77% at 48 hrs and approximately 59% at 72 hrs. At the same time, cell growth was measured. As a result, in melan-a cells, cell growth of indatraline-treated group was inhibited by 62% at 24 hrs and maintained by 56%, as compared to the control group. In B16-F10 cells, cell growth of indatraline-treated group was inhibited by 55% at 24 hrs and maintained by 54%, as compared to the control group (FIG. 5B).

7. Indatraline Inhibits Angiostenosis of In Vivo Model.

Autophagy-induced material has been studied to myocardial infarction which is occurred by accumulation of plaque in the inside of the blood vessels. According to previous studies, rapamycin (product name: sirolimus) known as autophagy-induced material shows effects for treating myocardial infarction, whereby further research continues to be vigorously.

Figure 6:
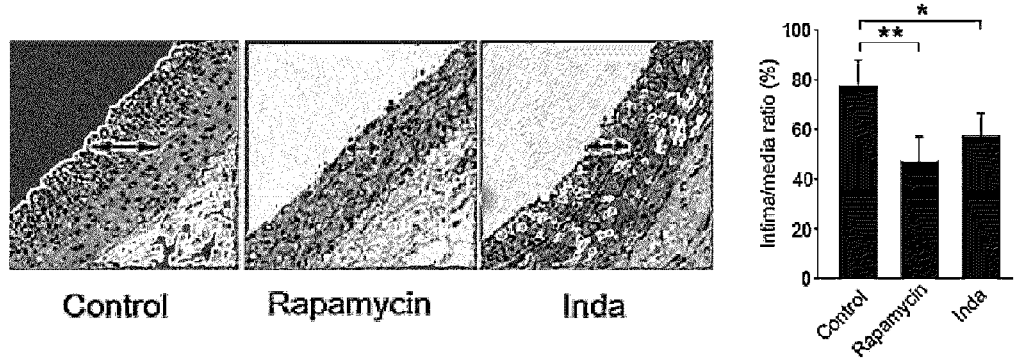
In FIG. 6, effects for inhibiting angiostenosis by indatraline and rapamycin in rat carotid artery were verified. After balloon injury, indatraline, rapamycin and DMSO (control group) were treated using catheter to observe accumulation of plaque in intima area. After 7 days, the ratio between intima area and media area was compared by observing tissue stenosed. As a result, smooth muscle cell growth in indatraline-treated group was reduced by approximately 20%, as compared to the control group (Mean Structural Equation Modeling. n=4, * P<0.05, ** P<0.001).

In the present invention, effects for inhibiting angiostenosis by indatraline as autophagy-induced material in rat carotid artery were verified. After balloon injury, indatraline, rapamycin and DMSO (control group) were treated using catheter to observe angiostenosis. After rapamycin or indatraline treatment, proliferation of smooth muscle cells was inhibited. As a result, it was determined that angiostenosis was significantly inhibited (FIG. 6). The ratio between intima area and media area was compared by observing tissue stenosed. As a result, intima area in control group accounted for approximately 80%, whereas intima area in indatraline-treated group was reduced by less than 60%. It would be found that indatraline inhibited stenosis of smooth muscle cells like rapamycin.

Discussion

Indatraline is a monoamine neurotransmitter inhibitor which effectively inhibits cell proliferation. The present study is newly reported that indatraline induces autophagy. Although the relationship between neurotransmitter inhibitor and autophagy has been studying, specific mechanisms for each neurotransmitter inhibitor have not yet been unknown. Indatraline-induced autophagy was verified by fluorescence screening and LC3 conversion immunoblotting. In addition, indatraline inhibits cell proliferation with an $IC_{50}$ of 3 µM in HeLa cell and an $IC_{50}$ of 0.5 µM in HUVEC cell, respectively. As shown in cell proliferation assay, extended treatment of indatraline (3 days) reduces rate of cell viability, however, there is no cytotoxicity during autophagy screening with treatment of 5 µM of indatraline in HeLa cell and HUVEC cell for 24 hrs. In addition, angiogenesis inhibitory effect of indatraline is tested as autophagy inducer and cell growth inhibitor. Indatraline of In vitro assay inhibits capillary formation, invasion and migration as angiogenesis indicators. Indatraline more effectively inhibits the invasion in HUVEC as compared to capillary formation and migration analysis. Since several angiogenesis inhibitors specifically inhibit invasion or metastasis, it may be an important property. Synthetically, autophagy inducer is a candidate for treating cancer, and indatraline in the present invention shows potential for anti-angiogenic agent. The exact mechanism of autophagy in relation to angiogenesis inhibition is not revealed. However, with further examination of indatraline, the relationship in monoamine neurotransmitter inhibitor, autophagy and angiogenesis could be revealed. Induction of autophagy may trigger signal inhibiting angiogenesis, or inhibition of neurotransmitter may simultaneously stimulate inhibitions of both of autophagy and angiogenesis. The exact mechanism of autophagy and angiogenesis is not revealed, a deep understanding for the mechanisms may be the cornerstone of the development of novel anti-angiogenic agent based on autophagy.

Autophagy in melanogenesis is a mechanism naturally induced by formation of melanosome. In melanoma, autophagy is actively induced for cell survival. However, indatraline has efficacy which induces autophagy and inhibits melanogenesis at the same time. i.e., it is supposed that autophagy-induced material such as indatraline activates autophagy with mechanism different from that of autophagy naturally occurring in melanogenesis. Neurotransmitter epinephrine has been already reported to have activity which induces melanogenesis and inhibits autophagy. From the connection of melanogenesis with the inhibitory activity to autophagy based on the previous study results, it would be anticipated that indatraline as monoamine neurotransmitter inhibitor is used to clarify a new correlation between melanogenesis and autophagy, enabling to develop agents for regulating melanogenesis.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCE

[1] M. Tsukada, Y. Ohsumi, Isolation and characterization of autophagy-defective mutants of Saccharomyces cerevisiae, FEBS Lett. 333, 169-174 (1993).

[2] Y. Ohsumi, Molecular dissection of autophagy: two ubiquitin-like systems, Nat. Rev. Mol. Cell. Biol. 2, 211-216 (2001).

[3] P. G. Clarke, Developmental cell death: morphological diversity and multiple mechanisms, Anat. Embryol. (Berl.) 181, 195-213 (1990).

[4] Mathew, R., Karantza-Wadsworth, V., and White, E., Role of autophagy in cancer. Nature Rev. Cancer, 7, 961-967 (2007).

[5] Martinez-Vincente, M., Talloczy, Z., Wong, E., Tang, G., Koga, H., Kaushik, S., de Vries, R., Arias, E., Harris, S., Sulzer, D., and Cuervo, A. M., Cargo recognition failure is responsible for inefficient autophagy in Huntington's disease. Nat. Neurosci., 13, 567-576 (2010).

[6] Matsuda, N., and Tanaka, K., Does impairment of the ubiquitin-proteasome system or the autophagy-lysosome pathway predispose individuals to neurodegenerative disorders such as Parkinson's Disease? J. Alzheimers Dis., 19, 1-9 (2010).

[7] Kondo, Y., Kanzawa, T., Sawaya, R., and Kondo, S., The role of autophagy in cancer development and response to therapy. Nature Rev. Cancer, 5, 726-734 (2005).

[8] Levine, B. and Kroemer, G., Autophagy in the pathogenesis of disease. Cell, 132, 27-42 (2008).

[9] Basrur, V., Yang, F., Kushimoto, T., Higashimoto, Y., Yasumoto, K., et al. Proteomic analysis of early melanosomes: identification of novel melanosomal proteins. J. Proteome Res., 2, 69-79 (2003).

[10] Smith, J. W., Koshoffer, A., Morris, R. E., and Biossy, R. E., Membranous complexes characteristic of melanocytes derived from patients with Hermansky-Pudlak syndrome type 1 are macroautophagosomal entities of the lysosomal compartment. Pigment Cell Res., 18, 417-426 (2005).

[11] Ganesan, A. K., Ho, H., Bodemann, B., Petersen, S., Aruri, J., Koshy, S., Richardson, Z., Le, L. Q., Krasieva, T., Roth, M., G., Farmer, P., and White, M. A., Genome-wide siRNA-based functional genomics of pigmentation identifies novel genes and pathways that impact melanogenesis in human cells. PLoS, 4, e1000298 (2008).

[12] Qu, X., Yu, J., Bhagat, G., Furuya, N., Hibshoosh, H., et al, Promotion of tumorigenesis by heterozygous disruption of the beclin 1 autophagy gene. J. Clin. Invest., 112, 1809-1820 (2003).

[13] Costin, G., E., and Hearing, V., J., Human skin pigmentation: melanocytes modulate skin color in response to stress. FASEB J., 21, 976-994 (2007).

[14] Sarangarajan, R., and Apte, S. P., Melanization and phagocytosic implications for age related macular degeneration. Mol. Vis., 11, 482-490 (2005).

[15] Zecca, L, Zucca, F. A., Albertini, A., Rizzio, E., Fariello, R. G., A proposed dual role of neuromelanin in the pathogenesis of Parkinson's disease. Neurology, 67, 58-71 (2006).

[16] Hyttel, J., and Larson, J. J., Neurochemical profile of LU 19-005, a potent inhibitor of uptake of dopamine, noradrenaline and serotonin. J. Neurochem. 44, 1615-1622, (1985).

[17-9] Biederbick, A., Kern, H. F., Elsasser, H. P., Monodansylcadaverine (MDC) is a specific in vivo marker for autophagic vacuoles. Eur J. Cell Biol., 66, 3-14 (1995).

[18] Seglen, P. O., and Gordon, P. B., 3-Methyladenine: specific inhibitor of autophagy/lysosomal protein degradation in isolated rat hepatocytes. Proc. Natl. Acad. Sci. USA, 79, 1889-1892 (1982).

[19] Yoshimori, T., Yamamoto, A., Moriyama, Y., Futai, M. and Tashiro, Y., Bafilomycin A1, a specific inhibitor of vacuolar-type H+-ATPase, inhibits acidification and protein degradation in lysosomes of cultured cells. J. Biol. Chem., 266, 17707-17712 (1991).

[20] Cerioni, L., Palomba, L., and Cantoni, O., The Raf/MEK inhibitor PD98059 enhances ERK1/2 phosphorylation mediated by peroxynitrite via enforced mitochondrial formation of reactive oxygen species. FEBS Lett., 547, 92-96 (2003).

[21] Blommaart, E. F. C., Krause, U., Schellens, J. P. M., Vreeling-Sindelarova, H., and Meijer, A. J., The phosphatidylinositol 3-kinase inhibitors wortmannin and LY294002 inhibit autophagy in isolated rat hepatocytes. Eur. J. Biochem., 243, 240-246 (1997).

[22] Kiselyov, A., Balakin, K. V., and Tkachenko, S. E., VEGF/VEGFR signalling as a target for inhibiting angiogenesis, Expert Opin. Investig. Drugs, 16, 83-107 (2007).

[23] Hu, D-N., Woodward, D. F., and McCormick, S. A., Influence of autonomic neurotransmitters on human uveal melanocytes in vitro, Exp. Eye Res., 71, 217-224 (2000).

[24] Seglen, P. O. and Bohley, P., Autophagy and other vacuolar protein degradation mechanisms, Experientia, 48, 158-172 (1992).

[25] Agar, N. and Young, A. R., Melanogenesis: a photoprotective response to DNA damage Mutation Res., 571, 121-132 (2005).

What is claimed is:

1. A method for treating a hypermelanosis, comprising administering to a subject having a hypermelanosis a pharmaceutical composition comprising (a) a pharmaceutically effective amount of a compound represented by the following Chemical formula 1 or a pharmaceutically acceptable salt thereof; and (b) a pharmaceutically acceptable carrier:

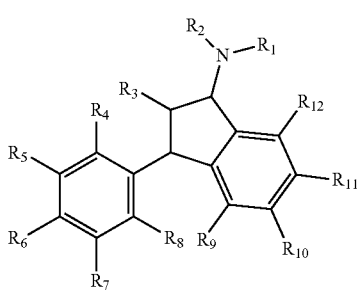

Chemical formula 1 wherein, each of $R_1$, $R_2$ and $R_3$ is independently hydrogen, hydroxy, $C_1$-$C_8$ alkyl, $C_1$-$C_8$ alkenyl and $C_3$-$C_8$ cycloalkyl or $C_1$-$C_8$ alkoxy, and each of $R_4$ to $R_{12}$ is independently hydrogen, halogen, hydroxy, $C_1$-$C_8$ alkyl, $C_1$-$C_8$ alkenyl and $C_3$-$C_8$ cycloalkyl or $C_1$-$C_8$ alkoxy.

2. The method according to claim 1, wherein each of $R_1$, $R_2$ and $R_3$ is independently hydrogen or $C_1$-$C_3$ alkyl, and each of $R_4$ to $R_{12}$ is independently hydrogen, $C_1$-$C_3$ alkyl or halogen.

3. The method according to claim 1, wherein the compound represented by the following Chemical formula 1 is a compound represented by the following Chemical formula 2:

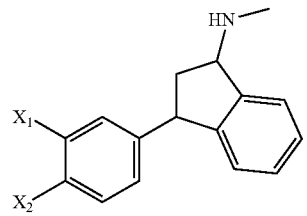

Chemical formula 2 wherein, each of $X_1$ and $X_2$ is independently halogen.

4. The method according to claim 3, wherein each of $X_1$ and $X_2$ is chlorine atom (Cl).

5. The method according to claim 1, wherein the hypermelanosis is selected from the group consisting of chloasma, freckle, age spot, blemish, epidermal melanocytic lesion, Cafe's au lait macules, Becker's Nevus, Nevus Spilus, Lentigines, dermal melanocytic lesions, Mongolian spot, Nevus of Ota, Acquired bilateral nevus of Ota-like macules, Nevus of Ito, Blue nevus, Melanocytic nevus, Junctional nevus, Compound nevus, Intradermal nevus, Halo nevus, Congenital nevocytic nevus, Spitz nevus, Dysplastic nevus, Melanoma, Lentigo maligna melanoma, Superficial spreading melanoma, Acral lentiginous melanoma, Nodular melanoma, pigment basal cell carcinoma, dermatofibromas, dermoid cyst, keloid and keratoacanthomas.

6. A method for whitening skin, comprising topically applying to a skin of a subject in need thereof a composition comprising a compound represented by the following Chemical formula 1 or a salt thereof:

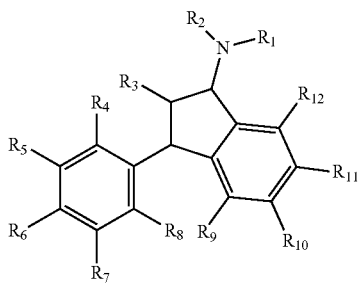

Chemical formula 1 wherein, each of $R_1$, $R_2$ and $R_3$ is independently hydrogen, hydroxy, $C_1$-$C_8$ alkyl, $C_1$-$C_8$ alkenyl and $C_3$-$C_8$ cycloalkyl or $C_1$-$C_8$ alkoxy, and each of $R_4$ to $R_{12}$ is independently hydrogen, halogen, hydroxy, $C_1$-$C_8$ alkyl, $C_1$-$C_8$ alkenyl and $C_3$-$C_8$ cycloalkyl or $C_1$-$C_8$ alkoxy.

* * * * *